US006623968B1

(12) United States Patent
Willson, III

(10) Patent No.: US 6,623,968 B1
(45) Date of Patent: *Sep. 23, 2003

(54) PARALLEL FLOW REACTOR AND APPARATUS FOR TESTING CATALYSTS

(75) Inventor: Richard C. Willson, III, Houston, TX (US)

(73) Assignee: University of Houston, Houston, TX (US)

( * ) Notice: Subject to any disclaimer, the term of this patent is extended or adjusted under 35 U.S.C. 154(b) by 224 days.

This patent is subject to a terminal disclaimer.

(21) Appl. No.: 09/612,857

(22) Filed: Jul. 10, 2000

Related U.S. Application Data

(62) Division of application No. 09/499,956, filed on Feb. 8, 2000, now Pat. No. 6,333,196, which is a division of application No. 08/664,836, filed on Jun. 17, 1996, now Pat. No. 6,063,633

(60) Provisional application No. 60/012,457, filed on Feb. 28, 1996.

(51) Int. Cl.$^7$ .............................................. G01N 31/10
(52) U.S. Cl. .................... 436/37; 250/281; 250/282; 250/288; 422/52; 422/62; 422/93; 422/196; 422/197; 436/147; 436/159; 436/161; 436/164; 436/172; 436/173
(58) Field of Search .......................... 250/281, 282; 422/62, 93, 104, 52; 436/37, 147, 159, 161, 164, 172–173

(56) References Cited

U.S. PATENT DOCUMENTS

| 3,010,880 A | 11/1961 | Littman et al. .......... 435/287.7 |
| 3,227,522 A | 1/1966 | Salisbury, Jr. et al. ... 435/288.3 |
| 3,431,077 A | 3/1969 | Danforth ................... 436/37 X |

(List continued on next page.)

FOREIGN PATENT DOCUMENTS

| CH | 430663 | * | 8/1967 |
| DE | 160855 | * | 4/1984 |
| DE | 234941 | * | 4/1986 |

(List continued on next page.)

OTHER PUBLICATIONS

M. R. Arnold et al, Ind. Eng. Chem. 1952, 44, 999–1003.*
M. I. Temkin et al, Kinet. Katal. 1969, 10, 461–463.*
K. Macak et al, Anal. Chem. 1969, 41, 3, 442–446.*
D. W. Bradley et al, Anal. Biochem. 1970, 33, 400–413.*
J. K. Musick et al, Ind. Eng. Chem., Process Des. Devel. 1972, 11, 350–354.*

(List continued on next page.)

*Primary Examiner*—Arlen Soderquist

(57) ABSTRACT

Apparatus for evaluating catalysts, including a multicell holder, e.g., a honeycomb or plate, or a collection of individual support particles, is treated with solutions/suspensions of catalyst ingredients to produce cells, spots or pellets holding each of a variety of combinations of the ingredients, is dried, calcined or treated as necessary to stabilize the ingredients in the cells, spots or pellets, then is contacted with a potentially reactive feed stream or batch, e.g., biochemical, gas oil, hydrogen plus oxygen, propylene plus oxygen, $CCl_2F_2$ and hydrogen, etc. The reaction occurring in each cell can be measured, e.g., by infrared thermography, spectroscopic detection of products or residual reactants, or by sampling, e.g., multistreaming through low volume tubing, from the vicinity of each combination, followed by analysis, e.g., spectral analysis, chromatography, etc., or by observing temperature change in the vicinity of the catalyst, e.g., by thermographic techniques, to determine the relative efficacy of the catalysts in each combination. Robotic techniques can be employed in producing the cells, spots, pellets, etc.

35 Claims, 6 Drawing Sheets

U.S. PATENT DOCUMENTS

| | | | |
|---|---|---|---|
| 3,474,004 A | 10/1969 | Fink | 435/288.3 |
| 3,536,452 A | 10/1970 | Norton et al. | 23/259 |
| 3,760,831 A | 9/1973 | Colvin | 137/117 |
| 3,770,027 A | 11/1973 | Guigan | 141/34 |
| 3,812,254 A | 5/1974 | McConnell | 424/226 |
| 3,819,490 A | 6/1974 | Klingstrom et al. | 435/287.7 |
| 3,881,872 A | 5/1975 | Naono | 23/253 R |
| 3,919,589 A | 11/1975 | Hanak | 315/71 |
| 3,933,044 A | 1/1976 | Loper et al. | 73/355 R |
| 3,943,363 A * | 3/1976 | Amblard | 250/288 |
| 4,099,923 A | 7/1978 | Milberger | 436/37 |
| 4,342,407 A | 8/1982 | Citrin | 222/485 |
| 4,626,412 A * | 12/1986 | Ebner et al. | 422/50 |
| 4,705,669 A | 11/1987 | Tsuji et al. | 442/93 |
| 4,728,502 A | 3/1988 | Hamill | |
| 4,996,387 A | 2/1991 | Gerhold et al. | 585/654 |
| 5,009,849 A * | 4/1991 | Ebner et al. | 422/83 |
| 5,024,992 A | 6/1991 | Morris | |
| 5,035,866 A | 7/1991 | Wannlund | 422/102 |
| 5,045,916 A | 9/1991 | Vor et al. | |
| 5,064,802 A | 11/1991 | Stevens et al. | 502/155 |
| 5,143,854 A | 9/1992 | Pirrung et al. | |
| 5,182,081 A | 1/1993 | Hedegaard et al. | 422/56 |
| 5,198,401 A | 3/1993 | Turner et al. | 502/155 |
| 5,200,023 A | 4/1993 | Gifford et al. | 156/626 |
| 5,262,130 A | 11/1993 | Kissel et al. | 422/311 |
| 5,281,540 A | 1/1994 | Merkh et al. | 436/530 |
| 5,288,514 A | 2/1994 | Ellman | |
| 5,304,354 A | 4/1994 | Finley et al. | 422/196 |
| 5,306,411 A | 4/1994 | Mazanec et al. | 204/265 |
| 5,318,935 A | 6/1994 | Canich et al. | 502/117 |
| 5,324,483 A | 6/1994 | Cody et al. | |
| 5,344,236 A | 9/1994 | Fishman | 374/5 |
| 5,356,756 A | 10/1994 | Cavicchi et al. | 430/315 |
| 5,364,765 A | 11/1994 | Abbott | 435/26 |
| 5,384,261 A | 1/1995 | Winkler et al. | 436/518 |
| 5,412,087 A | 5/1995 | McGall et al. | 536/24.3 |
| 5,424,186 A | 6/1995 | Fodor et al. | 435/6 |
| 5,587,128 A | 12/1996 | Wilding et al. | 422/50 |
| 5,595,712 A | 1/1997 | Harbster et al. | 422/129 |
| 5,670,322 A | 9/1997 | Eggers et al. | 435/6 |
| 5,677,195 A | 10/1997 | Winkler et al. | 436/518 |
| 5,679,548 A | 10/1997 | Barbas et al. | |
| 5,744,305 A | 4/1998 | Fodor et al. | 435/6 |
| 5,766,875 A | 6/1998 | Hafeman et al. | 435/29 |
| 5,776,359 A | 7/1998 | Schultz et al. | 252/62.51 |
| 5,847,105 A | 12/1998 | Baldeschwieler et al. | 536/25.3 |
| 5,852,498 A | 12/1998 | Youvan et al. | 356/417 |
| 5,859,700 A | 1/1999 | Yang | 356/300 |
| 5,914,245 A | 6/1999 | Bylina et al. | 435/19 |
| 5,959,297 A | 9/1999 | Weinberg et al. | 250/288 |
| 5,985,356 A | 11/1999 | Schultz et al. | 427/8 |
| 6,015,880 A | 1/2000 | Baldeschwieler et al. | 530/333 |

FOREIGN PATENT DOCUMENTS

| | | | | |
|---|---|---|---|---|
| EP | 0 260 469 B1 | 3/1988 | | H01J/49/02 |
| EP | 0 535 881 | 4/1993 | | |
| GB | 2176932 | 1/1987 | | |
| GB | 2194847 | 3/1988 | | |
| JP | 51-35687 | 3/1976 | | |
| JP | 07226884 | 8/1995 | | |
| WO | WO 90/00626 | 1/1990 | | |
| WO | WO 90/05746 | 5/1990 | | |
| WO | WO 90/15070 | 12/1990 | | |
| WO | WO 92/10092 | 6/1992 | | |
| WO | WO 93/09668 | 5/1993 | | |
| WO | WO 96/11878 | 4/1996 | | C01G/51/04 |
| WO | WO 98/55026 | 12/1998 | | A61B/10/00 |

OTHER PUBLICATIONS

E. D. Baily et al, J. Collooid Interface Sci. 1973, 45, 177–189.*
V. N. Goetz et al, Ind. Eng. Chem., Prod. Res. Develop. 1974, 13, 110–114.*
G. P. Korneichuk et al, Kinet. Katal. 1977, 18, 244–247.*
G. P. Korneichuk et al, Kinet. Katal. 1977, 18, 247–251.*
J. H. Stockinger et al, J. Chromatogr. Sci. 1978, 16, 418–426.*
P. J. Marteney U.S. Environ. Prot. Agency, Off. Res. Dev., EPA 600/7–79–038, Proc.: Workshop Catal. Combust. 1979, 3rd, 157–190.*
B. Kasemo Rev. Sci. Instrum. 1979, 50, 1602–1604.*
B. Kasemo et al, J. Catal. 1980, 66, 441–450.*
A. Golebiowski et al, Chem. Tech. 1982, 34, 36–38.*
M. Steininger et al, J. Chromatogr. 1982, 243, 279–284.*
Y. Barshad et al, J. Catal. 1985, 94, 468–477.*
J. G. Creer et al, Applied Catalysis 1986, 22, 85–95.*
J. W. Fulton Chem ical Engineering 1986, 93, 71–77.*
E. G. Butler et al, Anal. Biochem. 1988, 170, 402–408.*
H. Cui et al, Hebei Gongxueyuan Xuebao 1988, 17, 51–60.*
D. E. Rogers et al, Applied Catalysis 1989, 51, 181–194.*
Z. Kowalczyk et al, Applied Catalysis 1990, 58, 29–34.*
U. S. Ozkan et al, Applied Catalysis A 1993, 96, 365–381.*
Baiker, A. et al. Can. J. Chem. Eng. 1985, 63, 138–145.
Baldwin, 117 J. Amer. Chem. Soc. p. 5588.
Baum, R. M., C&E News Jan. 8, 1996 p. 20.
Belton, P.S. et al., Spectrochim. Acta, 1994, 50A, 689–696.
Bergbreiter, D.E. Chemtracts 1997, 10, 683–686.
Berkoff, C.E., et al. Chem. Industry 1981, 68–69.
Briceno, 270 Science 273–275 (1995).
Brown, J.R. et al. Springer Ser. Synergetics 1985, 29,86–95.
Burgess, K. et al. Angew. Chem. Int., Ed. Engl. 1996, 35, 220–222.
Business Week "Swapping a Test Tube for a Shotgun" Sep. 18, 1995.
Cai, G. et al. Huadong Huagong Xueyuan Xuebao 1987, 13, 432–437.
Cai, G. Huadong Huagong Xueyuan Xuebao 1982, 87–94.
Cai, G. Huadong Huagong Xueyuan Xuebao 1983, 579–582.
Cai, G. Ranliao Hugxeu Xuebao 1985, 13, 357–362.
Cai, G.C. Hua–tung Hua Kung Hsueh Yuan Hsueh Pao 1981, 115–124.
Cale, T.S. et al. J. Catal. 1983 79, 378–389.
Choudhary, V.R. et al. J. Catal. 1971, 23, 54–60.
D'Netto, G.A. et al. Inst. Chem. Eng. Symp. Ser. 1984, 84, 247–254.
Doppelbauer, J. et al. Appl. Phys. B 1983, 33, 141–147.
Fenniri, H. Curr. Med. Chem. 1996, 3, 343–378.
Govil A. et al. Hung, J. Ind. Chem. 1989, 17, 545–561.
Guyer Jr., A. Chimia 1967, 21, 134–135.
Hanak, J.J. J. Mater. Sci. 1970, 5, 964–971.
Hanak, J.J. RCA Technical Report, 1969.
Harold, M.P. et al. Chem. Eng. Sci. 1985, 40, 39–52.
Hill, C.L. et al. J. Mol. Catal. A: Chem. 1996, 114, 103–111.
Janda, K.D. et al. Proc. Natl. Acad. Sci. U.S.A. 1994, 91, 2532–2536.
Jensen, J.V. et al. Proc. Int. Congr. Catal. 6$^{th}$ vol. 2, G.C. Bond et al., ed., 1977, Chemical Society, 796–805.
Kauffman, S. Perspect. Drug Discovery Des. 1995, 2, 319–326.
Komarov, V.S. et al. Ablsorbts. Adsorbenty 1981, 9, 3–9.
Krevzer, D. et al., Appl. Catal. 1985, 15, 117–126.

Kul'kova, N.V. et al. Khim. Prom. 1968, 44, 656–658.
Langreth, R., Wall Street J., Sep. 11, 1995.
Leparlouer, P. et al. Thermochim. Acta 1986, 103, 21–26.
Lundgren, S. et al. Rev. Sci. Instrum. 1994, 65, 2696–2703.
MacBeath, G. et al. J. Am. Chem. Soc. 1994, 116, 6101–6106.
Machiels, C.J., ACS Symp. Ser. 1982, 178, 239–251.
McIntyre, N.S., et al. Surf. Rev. Lett. 1995, 2, 689–699.
Menger, J. Org. Chem. 1995, 60, 666–6667.
Moates, F.C. et al. Ind. Eng. Chem. Res. 1996, 35, 4801–4803.
Nessler 59 J. Org. Chem. 4723.
Ng, K.T. et al. J. Phys. Chem. 1976, 80, 2094–2102.
Posner, B. et al. Gene 1993, 128, 111–117.
Posner, B. et al. Trends Biochem. Sci. 1994, 19, 145–150.
Schuth, F. et al. J. Chem. Phys. 1990, 92, 745–756.
Sharma, S. et al. J. Catal. 1988, 110, 103–116.
Spitsyn, V.I. et al. Kinet. Katal. 1982, 23, 759–761.
Sudhak'ar, C. et al. Stud. Surf. Sci. Catal. 1993, 75, 1419–1430.
Sullivan, Today Chem. at Work, 14.
Tawfik, D.S. et al. Proc. Natl. Acad. Sci. U.S.A. 1993, 90, 373–377.
Van Wagner, J. et al. Stud. Surf. Sci. Catal. 1984, 19, 497–503.
Wenske, R., Tech. Umweltschutz 1976, 14, 169–197.
Xiang, 268 Science 1738.
Yamamoto, S.Y. et al. J. Chem. Phys. 1995, 103, 8209–8215.
Zingg, D.S. et al. J. Phys. Chem. 1980, 84, 2989–2906.
Anderson, J.A., J. Catal. 1993, 142, 153–165.
Barbas et al., "Assembly of Combinatorial Antibody Libraries on Phage Surfaces: The Gene III Site." *Proc. Natl. Acad. Sci.,* vol. 88 (Sep. 1991), pp. 7978–7982.
Blake, James and Litzi–Davis, Leonara, "Evaluation of Peptide Libraries: An Interative Strategy to Analyze the Reactivity of Peptide Mixtures with Antibodies." *Bioconjugate Chem.,* vol. 3, No. 6 (1992), pp. 510–513.
Bray et al. "The Simultaneous Multiple Production of Solution Phase Peptides; Assessment of the Geysen Method of Simultaneous Peptide Synthesis." *Tetrahedron Letters,* vol. 31, No. 40 (1990), pp. 5811–5814.
Bunin et al. "The Combinatorial Synthesis and Chemical and Biological Evaluation of 1,4–benzodiazepine Library." *Proc. Natl. Acad. Sci. USA,* vol. 91 (May 1994), pp. 4708–4712.
Clausen, B.S., et al., J. Catl. 1991, 132, 524–535.
Coq, B. et al. J. Molec. Catal. 1989, 55, 34–42.
Cwirla et al. "Peptides on Phage; A Vast Library of Peptides for Identifying Ligands." *Proc. Natl. Acad. Sci.,* vol. 87 (Aug. 1990), pp. 6378–6382.
Devlin et al. "Random Peptide Libraries: A Source of Specific Protein Binding Molecules." *Science,* vol. 249 (Jul. 27, 1990), pp. 404–406.
DeWitt et al., (1993) Proc. Natl. Acad. Sci. USA 90: 6909–6913, "Diversomers: An approach to nonpeptide, nonoligomeric chemical diversity".
DiSalvo, Francis J., "Solid–State Chemistry: A Rediscovered Chemical Frontier." *Science,* vol. 247 (Feb. 9, 1990), pp. 649–655.
Ellington, Andrew D. and Szostak, Jack W. "In Vitro Selection of RNA Molecules that Bind Specific Ligands." *Nature,* vol. 346 (Aug. 30, 199), pp. 818–822.

Faudon et al., J. of Catalysis 144: 460–471 (1993, "Properties of Supported Pd–Ni Catalysts Prepared by Coexchange and by Organometallic Chemistry".
Fawcett, T. CHEMTECH 1987, 17, 564–569.
Finnie, K.S., et al., Chem. Aust. 1993, 60, 180–182.
Fodor et al. Light–Directed, Spatially Addressable Parallel Chemical Synthesis. *Science,* vol. 2251 (Feb. 15, 1991) pp. 767–773.
Forrest, W.J., et al., Text of report presented at the "Infrared Detector Technology Workshop" held at NASA Ames Research Center Aug. 13–14, 1985, N87–13715.
Gallop et al., (1994) J. Med. Chem. 37 (9): 1233–1251, "Applications of Combinatorial Technologies to Drug Discovery. 1. Background and Peptide Combinatorial Libraries".
Gasiot et al., (1980), Nuclear Instruments and Methods 175: 96–97, "Multisample Thermoluminescence Reading".
Gates, B., "Summary of Accomplishments in DOE–Sponsored Project Entitled Metal–Support Bonds in Supported Metal", DOE/ER/13790—3, DE91 005004.
Georgiades et al. "IR Emission Analysis of Temperature Profiles in Pt/SiO2 Catalysts During Exothermic Reactions," *Angew. Chem Int. Ed. Engl.,* 26(10):1042–1043 (1987).
Geysen et al. "Strategies for Epitope Analysis Using Peptide Synthesis." *Journal of Immunological Methods,* 102 (1987), pp. 259–274.
Gordon et al, (1994) J. of Medicinal Chemistry 37 (10):1385–1401, "Applications of Combinatorial Technologies to Drug Discovery: 2. Combinatorial Organic Synthesis, Library Screening Strategies and Future Directions".
Gratton, L.M. et al., Appl. Spectrosc. 1978, 32, 310–316.
Hamilton et al., J. Am. Chem. Soc. (1986) 108: 5158–5167, "Coreceptor Molecules. Synthesis of Mettalloreceptors Containing Porphyrin Subunits and Formation of Mixed Substrate Supermolecules by Binding of Organic Substrates and of Metal Ions".*
Hanak (1975), Le Vide 175: 11–18, "Co–sputtering Its limitations and possibilities".*
Hanak et al., (1972), J. Appl. Phys. 43 (4): 1666–1673, "Calculation of Deposition Profiles and Compositional Analysis of Cosputtered Films".*
Hanak et al., (1976) RCA Review vol. 37: 220–233, "Model of Target Cross–Contamination During Co–Sputtering".*
Hanak et al., (1979), Presented at the 1979 Photovoltaic Solor Energy Conference, Berlin (west), "Optimization Studies of Materials in Hydrogenated Amorphous Silicon Solar Cells".*
Hanak, "Compositional Determination of rf Co–Sputtered Multicomponent Systems," *J. Vac. Sci. and Tech.,* 8(1):172–175 (1971).*
Hanak, "Electroluminescence in $ZnS:Mn_x$: $Cu_y$ rf–Sputtered Flims," *Japan J. Appl. Phy., Suppl. 2, Pt. 1,* pp. 809–812 (1974).*
Hanak, et al., "Calculation of Composition of Dilute Cosputtered Multicomponent Films," *J. Appl. Phys.,* 44(11): 5142–5147 (1973).*
Hanak, et al., "Radio–Frequency Sputtered Films of β–Tungsten Structure Compounds," *J. Appl. Phys.,* 41(12): 4958–4962 (1970).*
Hanak, et al., "The Effect of Grain Size of the Superconducting Transition Temperature of the Transition Metals," *Physics Letters,* 30A(3):201–202 (1969).*
Hanak, RCA Laboratories, "Automation of the Search for Electronic Materials by Means of Co–Sputtering".*

Hardisty et al. "Thermal Imaging in Electronics and Rotating Machinery," *British Journal of NDT*, 36(2):73–78 (1994).*

Hegedus et al., J. Amer. Chem. Soc. (1973) 95 (9), "Alkylation of Acid Halides by Alkyrhodium (I) Complexes".*

Hoffmann, (1981) Science 211 (4486): 995–1002, "Theoretical Organmetallic Chemistry".*

Hong, L. et al. J. Molec. Catal. 1992, 77, 273–282.*

Houghten et al. "Generation and Use of Synthetic Peptide Combinatorial Libraries for Basic Research and Drug Discovery." *Nature*, vol. 354 (Nov. 7, 1991), p. 84–86.*

Jansson, M. et al. J. Chromatgr. 1992, 626, 310–314.

Jonker, et al., *Physica*, XIX:120–130 (1953).

Kember, D.R., et al., J. Chem. Soc., Faraday Tans 2, 1981, 77 1321–1329.

Kiezel, L. et al. Chem. Stosow., Ser. A 1968, 12, 407–415. (and Translation).

Kobayashi, H., et al., Cat. Rev.—Sci. Eng., 10(2), 139–176 (1974).

Lam et al. "A New Type of Synthetic Peptide Library for Identifying Liband–binding Activity." *Nature*, vol. 354 (Nov. 7, 1994), pp. 82–84.

Leasure et al., (1994) Inorg. Chem. 33 (7): 1247–1248, "Photochemical Preparation of a Film–Based Catalyst with Spatial Control".

Lerner et al. "At the Crossroads of Chemistry and Immunology: Catalytic Antibodies." *Science*, vol. 242 (May 3, 1991) pp. 659–667.

Lewis, E.N., et al., Anal. Chem. 67, 3377–3381 (1995).

Liederman, D. et al. Prepr., Div. Pet. Chem., Am. Chem. Soc. 1973, 18, 15–32.

Lin et al., J. Am. Chem. Soc (1987), 109:4127–4129, "Models for Organometallic Molecule–Supported Complexes, Synthesis and Properties of Catonic Organometallics".

Lobban et al. "Standing Temperature Wave son Electrically Heated Catalytic Ribbons," *J. Phys. Chem.*, 93:733–736 (1989).

Mahendiran, et al., *Rev. Sci. Instrum.*, 66(4):3071–3072 (1995).

Markham, J.R., et al., Appl. Spectrosc. 1994, 48, 265–270.

Martin et al., (1993) Analytica Chimica Acta 281: 557–568, "Integrated enzyme reactor/detector for the determination of multiple substrates by images analysis".

Mazzarese, D., et al., J. Electron. Mater. 1992, 21, 329–333.

McClory, M.M. et al., J. Chem. Phys., 1986, 90, 628–633.

Mittasch, Advances in Catalysis and Related Subjects vol. II (1950) pp. 81–105.

Morita, Japanese Journal of Applied Physics Part 1–Regular Papers & Short, Notes, 1985, V24, N6, p723–727, "Improved Counter–Electrode Used in Two–Dimensional Electrochromic Writing Board".

Morrison, Jr., P.W., et al., J. Vac. Sci. Technol., A 1993, 11, 490–502.

N. Toshima Yuki Gosei Kagaku Kyokaishi 36, 909–916.

Needels et al. "Generation and Screening of an Oligonucleotide–encoded Synthetic Peptide Library." *Proc. Natl. Acad. Sci. USA*, vol. 90 (Nov. 1993), pp. 10700–10704.

Nogin, Yu. N. et al. Catal. Lett. 23, 79–86.

Ohlmeyer et al. "Complex Synthetic Chemical Libraries Indexed With Molecular Tags." *Proc. Natl. Acad. Sci. USA*, vol. 90 (Dec. 1993), pp. 10922–10926.

Parrish, W.J., et al., Infrared and Optoelectronic Materials and devices, SPIE vol. 1512, 68–77 (1991).

Pawlicki et al. "Spatial Effects on Supported Catalysts," *Chemical Engineering Progress*, pp. 40–45 (1987).

Pinilla, C., et al., Drug Development Research 33:133–145 (1994).

Pollack, Scott J. "Selective Chemical Catalysis by an Antibody." *Science*, vol. 234 (Dec. 19, 1986), pp. 1570–1573.

Prairie, M.R., et al., J. Catal., 1991, 129, 130–144.

Ramirez de Agudelo, M.M., et al. Chem. Eng. J. 1991, 46, 61–68.

Richardson et al., (1989) Applied Catalysis 48: 159–176, "Characterization and Deactivation of $NiO-ThO_2$".

Sarkany, J. et al. Appl. Spectrosc. 1982, 36, 320–322.

Scott, Jamie K. and Smith, George P. "Searching for Peptide Ligands with an Epitope Library." *Science*, vol. 249 (Jul. 27, 1990), pp. 286–390.

Seah et al., 1983 Practical Surface Analysis by Auger and X–ray Photolectron Sspectoscopy, "Chapter 1. A Perspective on the Analysis of Surfaces and Interfaces".

Jackel, D.P., DECHEMA Monographs vol. 132—VCH Verlagsgesellschaft 1995.

Stangl, R., et al., Proc.—SPIE 994, 2255, 685–696.

Takeuchi, M., et al., Shigen to Kankyo, 1995, 4, 429–434.

Tramontano et al. "Catalytic Antibodies." *Science*, vol. 234 (Dec. 19, 1986), pp. 1566–1570.

Tuerk, Craig and Gold, Larry. "Systematic Evolution of Ligands by Exponential Enrichment: RNA Ligands to Bacteriophage T4 DNA Polymerase." *Science*, vol. 249 (Aug. 3, 1990), pp. 505–510.

Uetsuka, H., et al., Surface Science 1996, 363, 73–78.

van Woerkom, P.C.M. et al., Appl. Optics, 1980, 19, 2546–2550.

Vassallo, A.M., et al., Appl. Spectrosc. 1992, 46, 73–78.

Vignes, S., et al., Compt. Rend. Congr. Ind. Gaz. 1961, 78, 405–411.

Voyatzis, R. et al. Energy Fuels 1994, 8, 1106–1114.

Wang, H., et al., Ceram. Trans. 1996, 74, 609–618.

Wangmaneerat, B., et al., Appl. Spectrosc., 1992, 46, 1447–1453.

Yamaguchi, et al., *Journal of the Physical Society of Japan*, 64(6):1885–1888 (1995).

Wu, Ching–Hsong; Hammerle, Robert H., "Development of a Low Cost, Thermally Stable, Monolithic Three–Way Catalyst System", *Ind. Eng. Chem. Prod. Ros. Dev.* 1983, 22, 559–585.

Hammerle, Robert H.; Wu, C.H., "Three–Way Catalyst Performance Characterization", Society of Automotive Engineers, Inc. 1981, 810275.

Falk, C.D.; Mooney, J.J., "Three–Way Conversion Catalysts: Effect of Closed–Loop Freed–Back Control and Other Parameters on Catalyst Efficiency", Society of Automotive Engineers, Inc. 1980, 800462.

Boguár, János, "Method for the Quantitative Evaluation of Catalytic Reactions: The Simultaneous Comparison Method", *Mikrochim. Ichnoanal. Acta*, 1963 (5–6), 801–828.

Research on the IJ, The History of the Amsterdam Lab, Shell Research B.V., Market Books B.V. Publishers, (1989) ISBN: 90 6593 106 6 [with translation].

Singoredjo, et al., "Selective Catalytic Reduction of NO With $NH_3$ Over Carbon Supported Copper Catalysts" *Catalysis Today*, 7 (1990) 157–165.

J.G. Creer et al., Applied Catalysis 22 (1986) Seiten 85–95.

J.J. Vajo et al., "Versatile Microreactor For Studies Of Gas–Surface Catalytic Reaction Between 10–7 and 10000 Torr;" Rev. Sci. Instrum. 56 (7), Jul. 1985.

* cited by examiner

VARIOUS DETECTORS

INFRARED DETECTOR
SPECTROSCOPIC DETECTOR
PHOTO METRIC DETECTOR
THERMOGRAPHIC DETECTOR
NIR, FTIR, FTNIR, DETECTOR
RAMAN DETECTOR

THERMAL TESTING

THERMAL
ELECTROCHEMICAL
FLAME IONIZATION
DETECTOR

LOW VOLUME TUBING

SPECTRAL
CHROMATOGRAPHIC
MS, NMR

OPTIONAL PRESSURE-TIGHT LEADS

PARALLEL FLOW REACTOR AND APPARATUS FOR TESTING CATALYSTS

This application is a divisional of U.S. Ser. No. 09/499,956 filed Feb. 8, 2000, and issued as U.S. Pat. No. 6,333,196, which is a divisional of U.S. Ser. No. 08/664,836 filed Jun. 17, 1996 and issued as U.S. Pat. No. 6,063,633, which itself claims the benefit of U.S. Ser. No. 60/012,457 filed Feb. 28, 1996.

BACKGROUND OF THE INVENTION

1. Field of the Invention

The present invention relates to the general field of catalyst testing, generally classified in U.S. Patent Class 502 or 252.

II. Description of the Prior Art

Prior Art will include C & E News, Jan. 8, 1996, p.30 which teaches reactive plastics, and the many catalyst testing devices and processes known to the petroleum refining art. F. M. Menger, A. V. Fliseev, and V. A. Migulin, "Phosphatase catalysts developed via combinatorial organic chemistry", J. Org. Chem. Vol. 60, pp 6666–6667, 1995. Xiang, 268 Science 1738 and Bricenol, 270 Science 273, both on combinatorial libraries of solid-state compounds; Sullivan, Today's Chem. At Work 14 on combinatorial technology; Nessler 59 J. Org. Chem. 4723 on tagging of combinatorial libraries; Baldwin, 117 J. Amer. Chem. Soc. 5588 on combinatorial libraries.

II. Problems Presented by Prior Art

Catalyst testing is conventionally accomplished in bench scale or larger pilot plants in which the feed is contacted with a catalyst under reaction conditions, generally with effluent products being sampled, often with samples being analyzed and results subjected to data resolution techniques. Such procedures can take a day or more for a single run on a single catalyst. While such techniques will have value in fine-tuning the optimum matrices, pellet shape, etc., the present invention permits the scanning of dozens of catalysts in a single set-up, often in less time than required for a single catalyst to be evaluated by conventional methods. Further, when practiced in its preferred robotic embodiments, the invention can sharply reduce the labor costs per catalyst screened.

SUMMARY OF THE INVENTION

General Statement of the Invention

According to the invention, a multisample holder (support) e.g. a honeycomb or plate, or a collection of individual support particles, is treated with solutions/suspensions of catalyst ingredients to fill wells in plates, or to produce cells, spots or pellets, holding each of a variety of combinations of the ingredients, is dried, calcined or otherwise treated as necessary to stabilize the ingredients in the cells, spots or pellets, then is contacted with a potentially reactive feed stream or batch e.g., to catalyze biochemical reactions catalyzed by proteins, cells, enzymes; gas oil, hydrogen plus oxygen, ethylene or other polymerizable monomer, propylene plus oxygen, or CC12F2 and hydrogen. The reaction occurring in each cell is measured, e.g. by infrared thermography, spectroscopic, electrochemical, photometric, thermal conductivity or other method of detection of products or residual reactants, or by sampling, e.g. by multistreaming through low volume tubing, from the vicinity of each combination, followed by analysis e.g. spectral analysis, chromatography etc, or by observing temperature change in the vicinity of the catalyst e.g. by thermographic techniques, to determine the relative efficacy of the catalysts in each combination. Robotic techniques can be employed in producing the cells, spots. pellets) etc. Each of these parameters is discussed below:

Catalysts: Biotechnology catalysts include proteins, cells, enzymes, etc. Chemical conversion catalysts include most of the elements of the Periodic Table which are solid at the reaction conditions. Hydrocarbon conversion catalysts include Bi, Sn, Sb, Ti, Zr, Pt, the rare earths, and many possible candidates whose potential has not yet been recognized for the specific reaction. Many synergistic combinations will be useful. Supported metals and metal complexes are preferred. The chemical catalysts can be added to the substrate (support) as elements, as organic or inorganic compounds which decompose under the temperature of the stabilizing step, depositing the element or its oxide onto the substrate, or as stable compounds.

Supports: Supports can be inert clays, zeolites, ceramics, carbon, plastics, e.g. reactive plastics, stable, nonreactive metals, or combinations of the foregoing. Their shape can be porous honeycomb penetrated by channels, particles (pellets), or plates onto which patches (spots) of catalyst candidates are deposited or wells in plates. Conventional catalyst matrix materials such as zeolites e.g. zeolite USY, kaolin, alumina, etc. are particularly preferred as they can simulate commercial catalysts.

Preparation: The catalyst candidate precursors can be deposited onto the supports by any convenient technique, preferably by pipette or absorbing stamp (like a rubber stamp), or silk screen. In preferred embodiments, the deposition process will be under robotic control, similar to that used to load multicell plates in biochemical assays. Many of the spots of catalyst will be built up by several separate depositions e.g. a channel penetrating a honeycomb can be plugged at one third of its length and the channel filled with a catalyst solution in its upper third, then the plug can be moved to the two-thirds point in the channel and a second catalyst pipetted in, then the plug can be removed and a third catalyst solution added, resulting in a channel in which reactants contact three catalysts successively as they flow through the channel. Catalyst can also be added by ion exchange, solid deposition, impregnation, or combination of these. The techniques of combinatorial chemical or biological preparation can preferably be utilized to prepare an array of candidate catalysts with the invention. Coprecipitates of two or more catalysts can be slurried, applied to the support, then activated as necessary. Catalysts can be silk screened onto a support plate or inside of a support conduit, and successive screenings can be used to add different catalyst combinations to different spots.

Stabilizing Step: Once the catalysts are in place on the support, any suitable technique known to the art can be used to stabilize, and/or activate the particular catalysts chosen, so they will remain in place during the reaction step. Calcining, steaming, melting, drying, precipitation and reaction in place will be particularly preferred.

Reactants: The Invention has utility with any reaction which can be enhanced by the presence of a catalyst, including biological reactions and inorganic and organic chemical reactions. Chemical reactions include polymerization reactions, halogenation, oxidation, hydrolysis, esterification, reduction and any other conventional reaction which can benefit from a catalyst. Hydrocarbon conversion reactions, as used in petroleum refining are an important use of the invention and include reforming, fluid catalytic cracking, hydrogenation, hydrocracking, hydrotreating, hydrodesulfurizing, alkylation and gasoline sweetening.

Sensors: The sensors used to detect catalytic activity in the candidate catalysts are not narrowly critical but will preferably be as simple as practical. Chromatographs, temperature sensors, and spectrometers will be particularly preferred, especially those adapted to measure temperature and/or products near each specific catalyst spot e.g. by multistreaming, multitasking, sampling, fiber optics, or laser techniques. Thermography, as by an infrared camera recording the temperature at a number of catalyst sites simultaneously, is particularly preferred. Other suitable sensors include NMR, NIR, TNIR, electrochemical, fluorescence detectors, Raman, flame ionization, thermal conductivity, mass, viscosity and stimulated electron or X-ray emission Sensors can detect products in a gas or liquid stream or on the surface of the support.

Endothermic reactions exhibit reduced temperature at best catalysts. Some sensors employ an added detection reagent, e.g. ozone to impart chemiluminesce.

Taggants: Optionally taggants (labels) can be added to identify particular catalysts, particularly where particles are employed as supports for the catalysts. These taggants can be conventional as discussed in the literature. Taggants can be chemicals which are stable at reaction conditions or can be radioactive with distinctive emissions. The techniques of combinatorial chemistry will be applicable with taggants as well as with catalysts chosen to suit the particular reaction to be enhanced by the catalyst.

Batch or Continuous: While the invention will be preferred on a flow basis, with reactants flowing by the catalyst spots under reaction conditions, batch testing e.g. in a stirred autoclave or agitated containers, can be employed, particularly in biological reactions.

Temperatures, pressures, space velocities and other reaction conditions: These will be determined by the reactants and reaction. Elevated pressures can be provided as reaction conditions by encasing the support in a reaction chamber with a sapphire or similar window for observation by the sensing means, or with pressure-tight leads extending through the reactor walls.

II. Utility of the Invention

The present invention is useful in the testing of catalysts for biotechnology, for promotion of gas phase and liquid phase reactions; under batch or, preferably, continuous flow-stream conditions; at elevated, reduced or atmospheric pressure; and saves both elapsed time and labor in screening for improved catalysts to promote a desired reaction.

DESCRIPTION OF THE PREFERRED EMBODIMENTS

EXAMPLE 1

Figure 1:
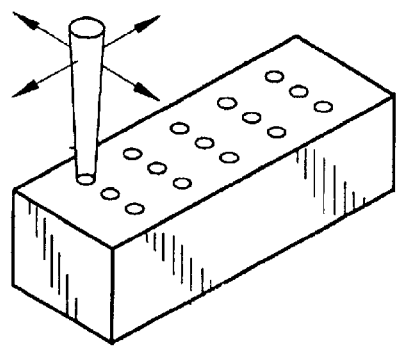
FIG. 1 is a schematic diagram of a preferred honeycomb support with a robotic pipetting device depositing different combinations of catalyst ingredients into each of the channels running through the honeycomb, which is thereafter calcined to stabilize the catalysts in each channel.
Figure 5:
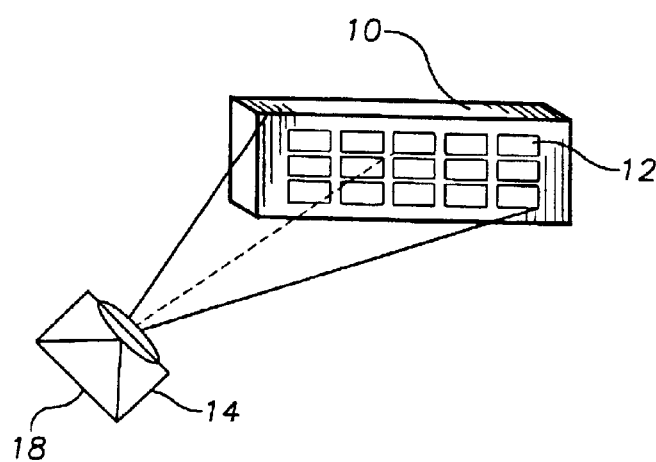
FIG. 5 shows schematically a sheet of support onto which 15 spots of different catalyst combinations have been deposited, as discussed in example 1.
Figure 6A:
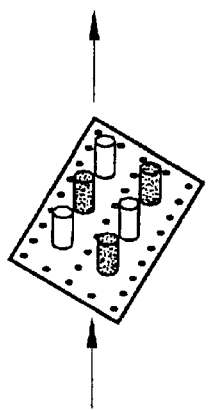
FIG. 6a shows an array of particles (pellets) of support in place in a reactor after having been ion exchanged with different catalyst combinations on different pellets (denoted schematically by different markings on the pellets in the Figure).
Figure 6B:
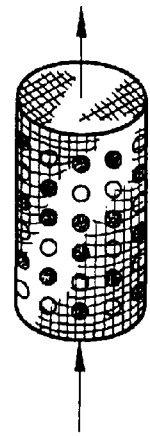
FIG. 6b shows a packed reactor which is less preferred because upstream pellets see fresh feed, while downstream pellets see partially reacted feed.
Figure 7:
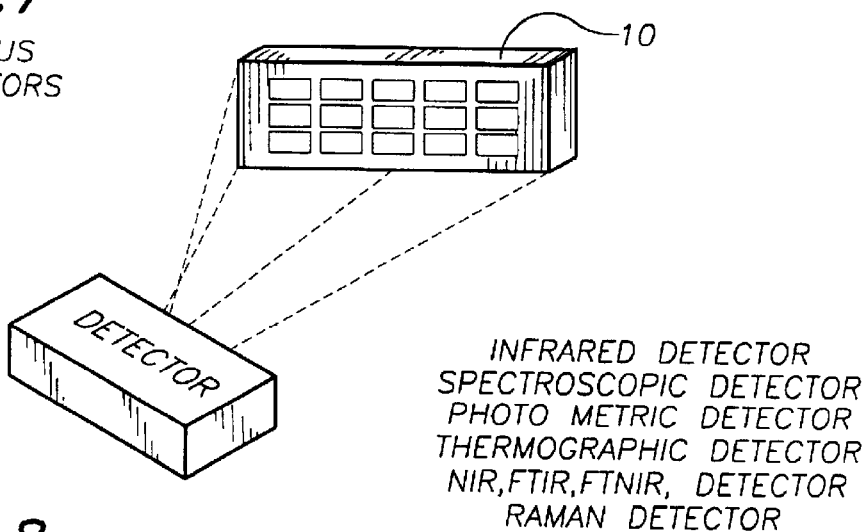
FIG. 7 shows schematically the use of various detectors on the candidate catalyst array of FIG. 5.
Figure 8:
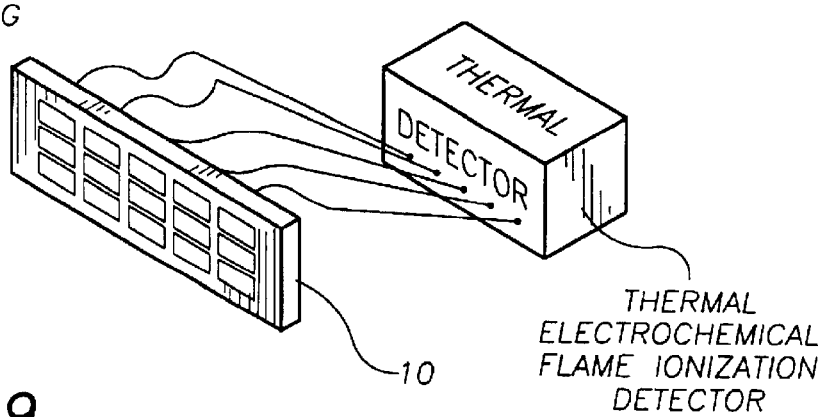
FIG. 8 shows schematically the use of thermal, electrochemical, flame ionization, etc. detectors on the candidate catalyst array of FIG. 5.
Figure 9:
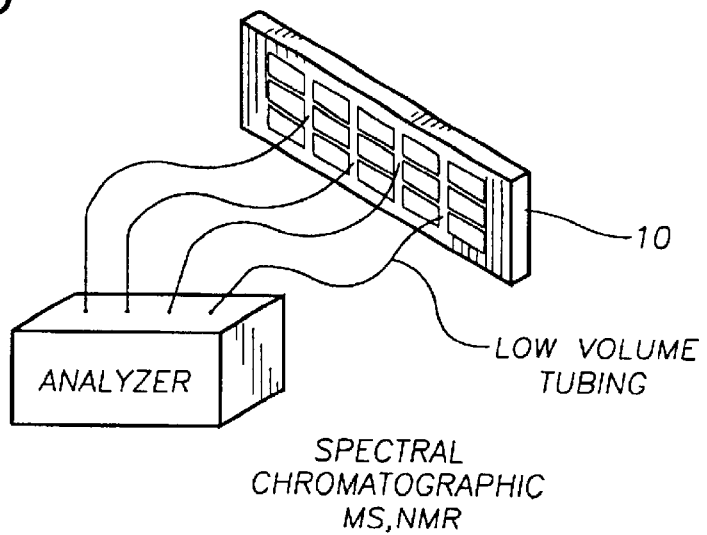
FIG. 9 shows schematically the use of low volume sampling tubes with various analyzers on the candidate catalyst array of FIG. 5.

Referring to FIG. 1, a sheet of alpha alumina 10 is wash-coated with particles of porous gamma-alumina by standard methods. Solutions of oxalate salts of 12 different transition metal elements are prepared in the wells of a 24 well microtiter dish made of polystyrene. A Beckman Biomek 2000 robotic automated liquid handling system is used to prepare dilutions and mixtures from the original stocks, again in the wells of microtiter style plates. The robot is used to deposit 20 microtiter aliquots of each of the resulting solutions at defined positions (spots) 12 on the surface of the alumina support 10, which is then dried, calcined and inserted into a reactor capable of temperature control at temperatures from 100 to 350 degrees centigrade. After reduction, a potentially reactive mixture of oxygen and hydrogen is fed to the reactor. An Agema infrared sensitive camera 14 is used to observe the alumina support through infra-red-transparent sapphire windows 16 shown in FIG. 11, via a polished metal mirror. The camera is set so that the lower end of its dynamic range corresponds to a temperature of about 40 degrees C. below the feed temperature and the maximum signal is associated with a temperature about 200 degrees higher. Compositions catalyzing the reaction are revealed by the localized temperature increases (decreases for endothermic reactions) around spots 12 of that composition, as shown on photograph 18 in FIG. 5.

Example 1a

Catalysts are alternatively identified by conducting the reaction in the presence of strong ultraviolet and/or visible light illumination. with infrared thermography being conducted immediately after the illumination is turned off, or through the use of a short pass filter on the illumination source to eliminate contaminating infra-red radiation.

EXAMPLE 2

Figure 2:
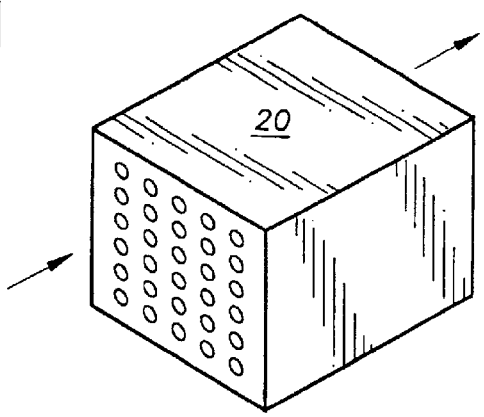
FIG. 2 is shows schematically the honeycomb of FIG. 1 being contacted by reactants flowing through the channels.

Referring to FIG. 2, a porous alumina monolith 20 (Corning) having square or circular cross-section channels extending in a regular array through its entire thickness is treated in each channel with a solution of catalyst precursors of differing compositions, with each composition being segregated in its own channel. After drying, calcination, etc., the activated monolith is placed in contact with a flowing potentially reactive mixture at an elevated temperature, and observed in the infra-red using an Agema model camera. The enthalpy of reaction produces localized temperature differences in the vicinity of compositions exhibiting catalytic activity and these are observed as temperature variations near the exits of the channels.

EXAMPLE 3

Figure 3A:
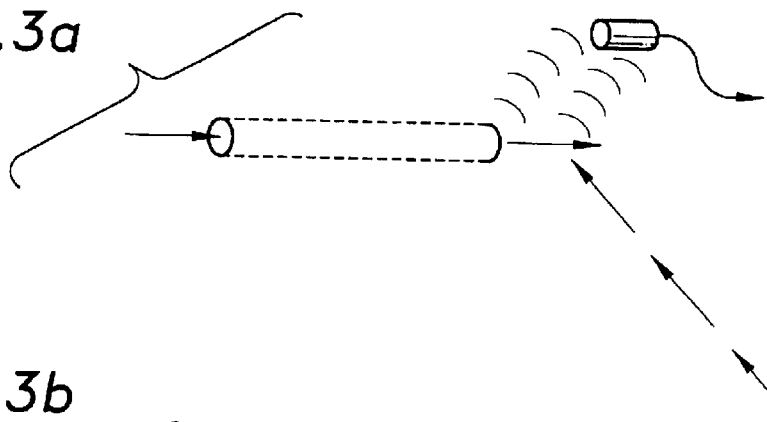
FIGS. 3a and 3b are alternative schematic diagrams of one channel of the honeycomb of FIG. 2 with a detector sensing the products exiting the channel by measuring absorption in a laser beam directed through the products or the channel.
Figure 3B:
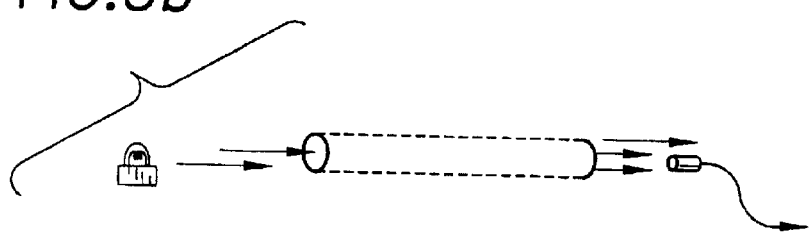
Figure 4A:
FIG. 4a shows a channel plugged at its midpoint prior to receiving a solution of catalyst and FIG. 4b shows the plug moved to the end of the channel, so as to form a channel having one catalyst in one half its length and another catalyst in its other half.
Figure 4B:

Referring to FIG. 3, a porous ceramic monolith 20 of the type described in Example 2, bearing various catalyst compositions in its channels is installed in a reactor (not shown) in such a way that the entire length of each channel can be observed through sapphire windows at the ends of the reactor. A broad-spectrum thermal infrared source is installed at one end of the reactor, giving an areal infrared energy flux density. An Agema IR-sensitive camera is positioned in such a way as to observe the infra-red source directly through a significant fraction of the pores. An interferometric or other filter is installed on one side of the reactor between the camera and the infra-red source such that the light reaching the camera from the source is substantially limited to wavelengths between 4 and 4.5 microns. Observation of absorbency at this wavelength range is used to compare candidate catalyst compositions on the basis of their production of carbon dioxide, an undesired side product of the intended reaction. Catalyst compositions chosen for low carbon dioxide formation (in combination with high overall conversion activity as measured by infra-red absorbance of the desired product or by infrared thermography) are found to have high selectivity for the desired product over the carbon dioxide side product.

EXAMPLE 4

A collection of catalyst precursor compositions is produced by automated liquid handling device, and a catalyst support particle is contacted with each composition. After further treatment to stabilize and activate the catalyst precursors, catalyst pellets are arrayed on a surface, exposed to a potentially reactive environment and their activity determined by infrared thermography.

EXAMPLE 5

Solutions of combinations of catalyst precursors are prepared in a variety of separate vessels. Each composition also contains a small quantity of a labeling material (e.g., stable isotopes of the element carbon or sulfur in varying ratios). Catalyst support particles are contacted with catalyst precursor preparations, and activated. Pellets are then contacted one at a time with a potentially reactive mixture (for example, by elutriation into an enclosed volume) and their activity measured (by thermography, by spectroscopic measurement of products, or sampling of the surrounding vapor or liquid phase). Particles showing activity are collected and individually analyzed for their content of the labeling material so as to determine the composition giving the desired catalytic activity.

EXAMPLE 6

Example 2 is repeated except that only a portion of the pore length is coated with a catalyst candidate so as to allow for observation of unmodified monolith pore wall as a control reference standard for optical uniformity.

EXAMPLE 7

The emissivity of the support monolith pores of the support 20 of Example 2 is mapped at a wavelength of interest by holding the monolith at the intended experimental temperature in reactants. Digitally stored maps of the emissivity are used to normalize the infrared energy flux measured under experimental conditions, to improve the accuracy with which local temperatures can be estimated.

EXAMPLE 8

A surface of high, substantially uniform emissivity is located at the end of the monolith of Example 2, away from the camera, in close radiative heat transfer/contact with the monolith channel material. The temperature of the portion of the surface closest to the open end of each channel is observed. In this case, it is necessary that gas be admitted into the channels past the uniform radiative surface, either by means of pores or by means of a small offset between the radiative surface and the monolith.

EXAMPLE 9

Figure 10:
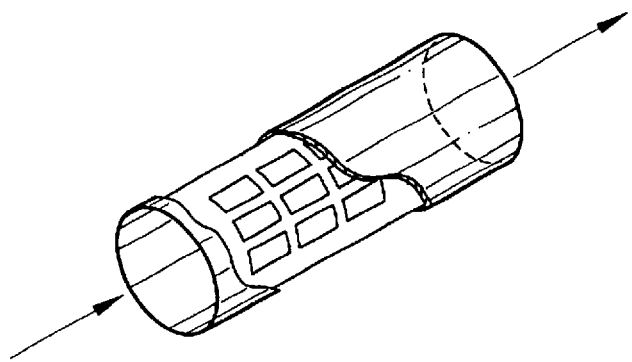
FIG. 10 shows schematically the use of a candidate catalyst array deposited on the interior of a monolith.

Alternatively, spots of catalysts can be deposited on the inner surface of a reactor e.g. a tube formed of the support material as shown in FIG. 10, and temperature of the corresponding spots on the outside of the reactor can be measured to determine by conduction whether the respective catalyst has increased or decreased in temperature under the reaction.

EXAMPLE 10

The process of Example 1 is repeated except that the reactants are in the liquid phase and a liquid phase assay is used (FIG. 12) to detect the activity of individual catalyst candidates.

EXAMPLE 11

The experiment of Example 4 is repeated except that the metal loading is directly measured by dissolving the pellet and directly analyzing the metal loading.

EXAMPLE 12

Figure 11:
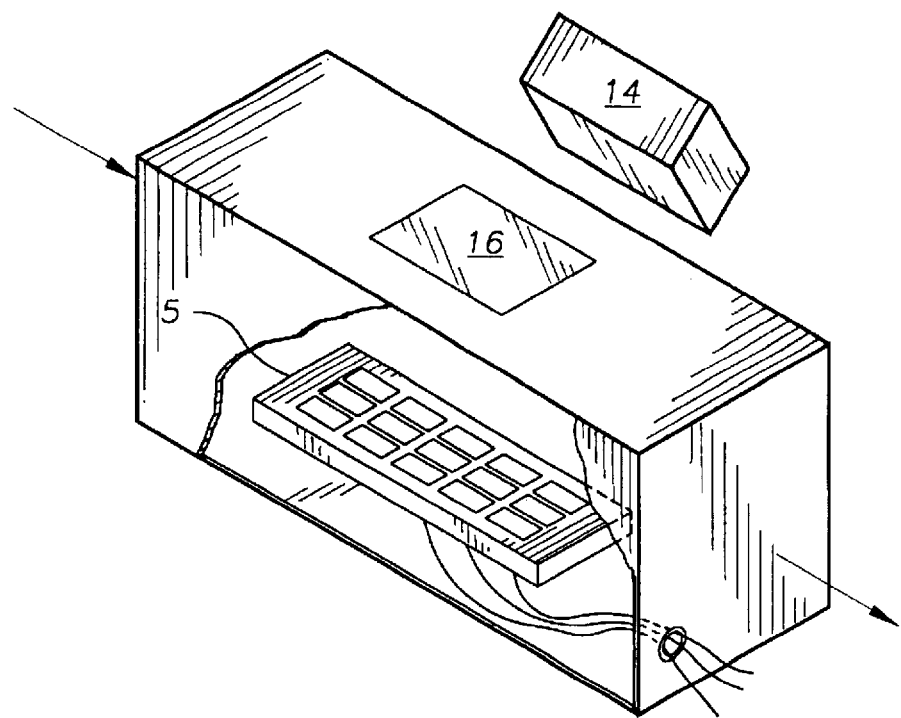
FIG. 11 shows schematically the use of a flow reactor with sapphire window open to various detectors on the candidate catalyst array of FIG. 5, and shows optional pressure tight electrical leads 13 for leading to a detector.
Figure 12:
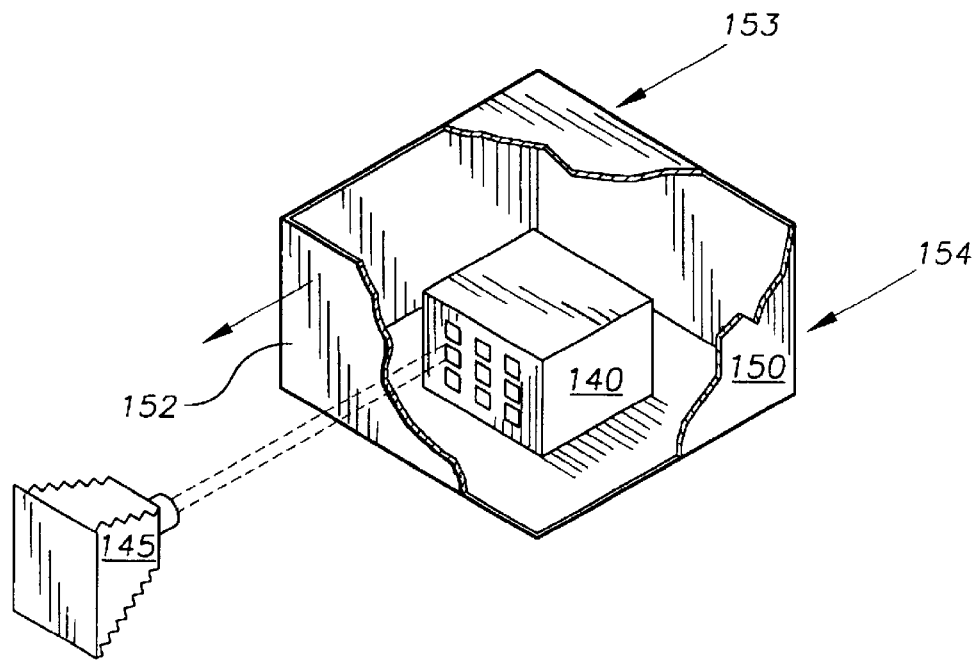
FIG. 12 shows schematically the apparatus of Example 13.

A sheet of alpha alumina 5 in FIG. 12, is wash coated with particles of porous gamma-alumina by standard methods. Solutions of oxalate salts of 12 different transition metal elements are prepared in the wells of a 24 well micro titer dish made of polystyrene. A Beckman Biomek 2000 automated liquid handling system is used to prepare dilutions and mixtures of the original stocks, again in the wells of microtiter style plates. The Biomek robot 6 is used to deposit 40 microliter aliquots of each of the resulting solutions at defined positions on the surface of the alumina support, which is then dried, calcined and inserted into a reactor (as shown in FIG. 11) controlled at a temperature of 200 degrees centigrade. A gaseous mixture of hydrogen (97.5%) and oxygen (2.5%) is fed at a temperature of 200 degrees centigrade. Using the apparatus of FIG. 11, an infra-red sensitive camera 14 is used to observe the alumina support through infra-red-transparent sapphire windows 16. The camera is set so that its lower range corresponds to the feed temperature and the maximum signal is associated with a temperature degrees 20 degrees higher. Compositions catalyzing the reaction are revealed by the localized temperature increases around spots of that composition.

EXAMPLE 13

A porous alumina monolith 140 in FIG. 12, having square pores extending in a regular array through its entire thickness at a density of 25 per square inch is washcoated with alumina particles. The channels are then partially filled with solutions of differing compositions, each containing one or more metal oxalate or nitrate salts, with each composition being segregated in its own channel or set of channels. After drying and activation in the presence of hydrogen gas, the activated monolith is placed into a sapphire-window-equipped reactor 150 in which it can be observed in the infrared using an IR-sensitive camera 145. The camera is positioned in such a way as to observe the walls of the support. The relative emissivity of the support at each pixel is determined by imaging the monolith in the IR while holding the reactor and monolith at each of several constant temperatures while flowing nitrogen gas 153 through the reactor. The reactor is then fed with a gas mixture of 2.5 mole % oxygen in hydrogen 154. The reactor and feed temperatures are originally set to 40 degrees centigrade, and are gradually increased While the catalyst-bearing monolith is repeatedly imaged in the IR. The temperature in each cell may be judged by observing the cell at a position adjacent to the end of the catalyst-precursor-coated section of the channel, or by normalizing the observed IR energy emission by the emissivity calculated from the images taken under nonreactive conditions. The compositions in the cells showing the earliest temperature increase above the reactor temperature are useful as hydrogen oxidation catalysts.

EXAMPLE 14

Figure 13:
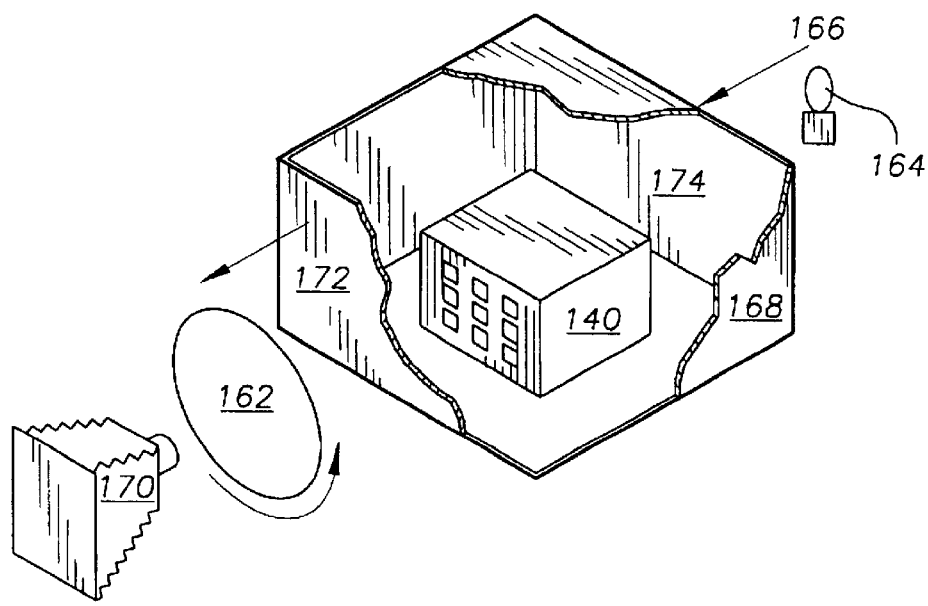
FIG. 13 shows schematically the apparatus of Examples 14 and 16.
Figure 14:
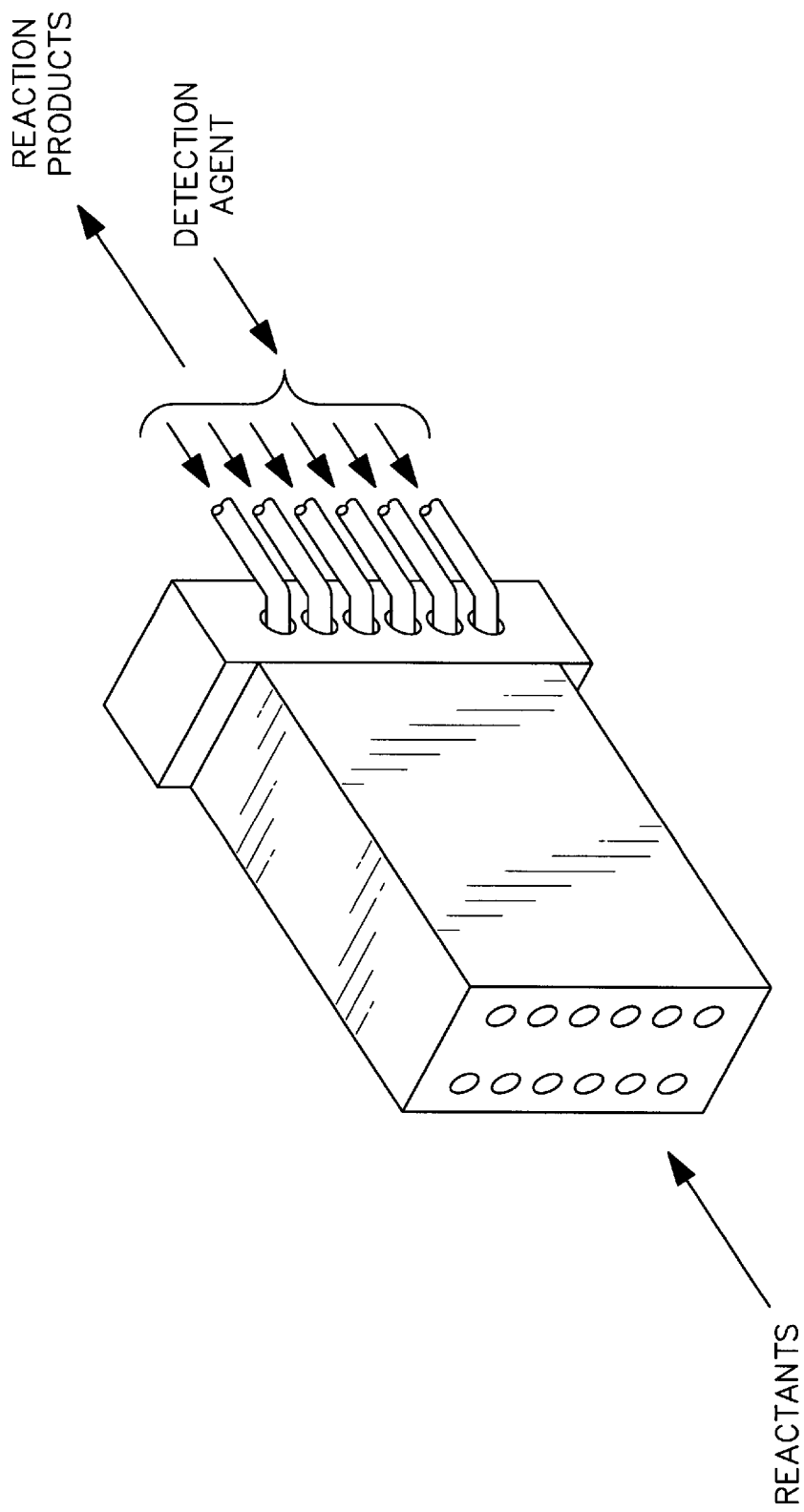
FIG. 14 shows schematically an embodiment having an array of tubes for introducing a detection agent in the product-containing streams, as described for example, in Example 22.

A porous alumina monolith 140 in FIG. 13 having square channels in a regular array extending through its entire 10 centimeter thickness at a density of 25 per square inch is washcoated with alumina particles. The channels are then partially filled with solutions of differing compositions, each containing one or more metal salts and in some cases also candidate modifiers such as barium, cesium or potassium compounds, each composition being segregated in its own channel or set of channels.

After drying and reduction in the presence of hydrogen gas, the activated monolith is placed into a reactor in which it can be observed through a sapphire window 172 using an IR-sensitive camera 170.

This first window 172 is positioned 0.5 centimeter from the surface of the monolith. The camera 170 is positioned in such a way as to look through the window 172, through the channels of the support and through a second sapphire window 174 toward a source of IR radiation 164.

The reactor 168 is then fed with methane gas, mixed with oxygen and argon, in such a way that the gas 165 flows through the channels of the monolith toward the camera. An optical filter 162 which selectively passes IR radiation at 4.3 microns, a wavelength which is strongly absorbed by carbon dioxide, is inserted between the IR source and the camera. The effective concentration of carbon dioxide in each channel is inferred from the IR intensity at 4.3 microns seen in that channel. The reading at 4.3 microns for each pixel is divided by the reading taken through a filter selective for an IR wavelength which is near 4.3 microns, but which is not absorbed strongly by carbon dioxide, methane or water, to compensate for potential optical artifacts.

Compositions giving high concentrations of carbon dioxide after long exposures to operating conditions are useful in catalytic oxidation of methane.

EXAMPLE 15

Solutions of combinations of catalyst precursors are prepared in a variety of separate vessels. Each composition also contains a small quantity of a labeling material (e.g., stable isotopes of the element sulfur in varying ratios unique to each composition). Catalyst support particles are contacted with the preparations of catalyst precursor compositions, and activated. Pellets are then contacted one at a time with a potentially reactive mixture (for example, by elutriation into an enclosed volume) and their activity measured (by thermography, by spectroscopic measurement of products, or sampling of the surrounding vapor or liquid phase). Particles showing activity are collected and individually analyzed for their content of the labeling material so as to determine the composition giving the desired catalytic activity.

EXAMPLE 16

A Teflon block monolith 140 in FIG. 13, having square channels in a regular array extending through its entire thickness at a density of 9 per square inch is prepared in such a way that a shallow well exists at the bottom of each channel. Each well is charged with a different polymer preparation bearing sulfonic acid groups on its surface, and a porous retaining mesh installed to keep the polymer samples in place.

The catalyst-charged monolith is placed into a reactor in which it can be observed through a window 172, positioned 0.5 centimeter from the surface of the block. A camera 170 is positioned in such a way as to look via through the sapphire window, through the channels of the support and through a second window 174, toward a source of polarized light 164. A polarizer 162 is installed between the block and the camera.

A sucrose solution 166 is fed to the reactor in such a way as to flow through the channels of the block. The angle of rotation of polarized light in passing through the liquid in each channel is measured by rotating the polarizer to various angles, and observing the variation in brightness of the light passing through each channel. The candidate catalysts found in channels giving the greatest change in the angle of rotation are useful as catalysts of sucrose hydrolysis.

EXAMPLE 17

Catalysts for photooxidation of hexane are identified by conducting the reaction in the apparatus of Example 16 in the presence of strong ultraviolet and/or visible light illumination, with infra-red thermography being conducted immediately after the illumination is turned off, or through the use of a short pass filter on the illumination source to eliminate contaminating infrared radiation.

EXAMPLE 18

Samples of cyanogen bromide-activated cross linked agarose beads are exposed to solutions of alcohol oxidase at varied pHs, salt concentrations, and enzyme concentrations. After coupling of the enzyme, residual active groups are quenched with ethanolamine, the beads are washed, and each sample placed in a separate well of a multiwell plate. The plate is exposed to a flowing air stream containing ethanol vapor and observed with an Amber infrared-sensitive camera.

The samples showing the greatest temperature increase are selected as highly active immobilized alcohol oxidase catalysts.

EXAMPLE 19

Samples of cyanogen bromide activated cross linked agarose beads are exposed to solutions of anti-alcohol oxidase antibodies at varied pHs, salt concentrations, and antibody concentrations. After coupling of the enzyme, residual active groups are quenched with ethanolamine. The beads are washed, exposed to a solution of alcohol oxidase) washed again, and each sample placed in a separate well of a multlwell plate. The plate is exposed to a flowing air stream containing ethanol vapor and observed with an Amber infrared-sensitive camera.

The samples showing the greatest temperature increase are selected as highly active immobilized alcohol oxidase catalysts.

EXAMPLE 20

A ceramic monolith having channels arranged in perpendicular row/column format passing through its entire thickness is washcoated with porous alumina particles and all the channels in each column are treated with the same catalyst precursors, which are activated. A potentially-reactive stream is flowed through the channels of the monolith, and a multiwavelength beam of radiation is passed over the surface of the monolith, parallel to each column, to a detector situated at the end of the column. The composition of the stream leaving the pores in that column is estimated by processing the detector output, including Fourier transformation and/or weighted summation/differencing of the intensities at different wavelengths.

EXAMPLE 21

Pellets bearing catalytically-active groups capable of catalyzing the conversion of both the D- and L- stereoisomers of a reactant are treated with a variety of substances potentially capable of preferentially suppressing (temporarily or permanently) the conversion of the L-stereoisomer of that compound by that catalyst. The pellets are distributed among the wells of a multiweli plate and exposed to a mixture of the isomers of the compound to be modified. Pellets treated with the suppressor giving the greatest reduction in the activity for conversion of the L-isomer are useful in stereoselective modification of the D-isomer.

EXAMPLE 22

A ceramic monolith having channels arranged in perpendicular row/column format passing through its entire thickness is washcoated with porous alumina particles and the channels treated with catalyst precursors, which are activated. A potentially-reactive stream is flowed through the channels of the monolith. A manifold consisting of an array of tubes, each smaller than the dimensions of an individual channel, is used to introduce a stream containing ozone into the stream flowing through each channel, near its outlet.

Reaction of the introduced ozone with the desired product liberates light, which is detected by a camera directed at the monolith. The catalyst composition giving the strongest light output is a useful catalyst for conversion of the reactants to the ozone-reactive desired product.

EXAMPLE 23

A ceramic monolith having channels arranged in perpendicular row/column format passing through its entire thickness is washcoated with porous alumina particles and the channels treated with catalyst precursors, which are activated and then exposed to a potentially deactivating substance. A potentially-reactive stream is flowed through the channels of the monolith. A manifold consisting of an array of tubes, each smaller than the dimensions of an individual channel 71 is used to sample the stream flowing within each channel. Samples from each channel in turn are introduced into a gas chromatograph-mass spectrometer combination through an arrangement of switching valves, and catalyst compositions giving the highest yield of desired products are useful in conversion of that reactive stream.

Modifications

Specific compositions, methods, or embodiments discussed are intended to be only illustrative of the invention disclosed by this specification. Variations on these compositions, methods, or embodiments are readily apparent to a person of skill in the art based upon the teachings of this specification and are therefore intended to be included as part of the inventions disclosed herein. For example, statistically-designed experiments, and automated, iterative experimental process methods can be employed to obtain further reductions in time for testing. Attachment/arraying of preformed catalytic elements (especially precipitates, also single molecules and complexes such as metallocenes) onto a support, preferably by precipitating or deposition is useful in many cases.

Detection can involve addition of some reagent to the stream leaving each candidate, the reagent allowing detection of a catalyst product through staining or reaction to give a detectable product, light, etc.

The supports can comprise arrays with special arrangements for e.g., a header of multiple delivery tubes for uniform flow distribution, inserted into each channel in a block.

The detection means can comprise electrochemical means, or a gamma camera for metals accumulation measurement, imaging elemental analysis by neutron activation and imaging by film or storage plate of emitted radioactivity, temperature measurement by acoustic pyrometry, bolometry, electrochemical detection, conductivity detection, liquid phase assay, preferably dissolving the support pellet and directly analyzing the metal loading; measuring refractive index in the liquid phase; observing the IR emissions of product gases directly, without the usual source and using instead the radiation hot gases emit at characteristic wavelengths.

Other modifications can include testing for selectivity after deliberately poisoning some sites, especially in chiral catalysis, etc. The formulations can be supported in the form of spots or layers on the surface of a support containing wells or channels or channels extending across the entire extent of the support. The support can comprise a form of carbon, zeolite and/or plastic. The plastic can comprise a reactant. The support can hold a form of catalyst made by coprecipitation, or aluminum, or particles.

At least one of the formulations can preferably comprise a material selected from the group consisting of transition metals, platinum, iron, rhodium manganese, metallocenes, zinc, copper, potassium chloride, calcium, zinc, molybdenum, silver, tungsten, cobalt and mixtures of the foregoing.

The label can comprise different isotopes or different mixtures of isotopes.

The reaction conditions can comprise a pressure greater than one bar absolute pressure and the contact can be at a temperature greater than 100 degrees centigrade The method can comprise detection of temperature changes in the vicinity of a respective formulation due to reaction endotherm or exotherm.

The method can comprise treatment with a reducing agent. The contacting step can be carried out in the presence of compounds which modify the distribution of the metal within the porous support.

The candidate catalyst formulations can be contacted in the form of spots or layers on the surface of a support containing a washcoat supported by an underlayer.

The stabilizing step can be carried out with a temperature gradient or other means whereby certain candidate catalyst formulations are exposed to different temperatures. The stabilizing can comprise calcining, steaming, drying, reaction, ion exchange and/or precipitation.

The detection of temperature changes due to reaction can employ a correction for emissivity variations associated with differences in chemical composition.

The array of formulations to be tested can comprise preformed metallocenes or other catalytic complexes fixed to a support.

The infrared radiation can be detected through the use of nondispersive infrared spectroscopy, or infrared-sensitive photographic film. The detector means can comprise means for physically scanning over an array of candidate formulations.

Observations at multiple wavelengths can be processed by mathematical manipulation e.g. transformation, weighted summation and/or subtraction, etc.

Reaction activity, reactants, or products can be detected through the use of an added reaction which signals the presence of reaction or particular compounds or classes of compounds.

Chemiluminescence can be used as an indicator of reaction activity, or particular compounds or classes of compounds.

A substantially collimated radiation source can be employed in product detection/imaging.

Multi-tube sampling can be used to lead into a mass spectrometer, chromatograph, or optical monitor.

To simulate aging, etc., the formulations can exposed to a deleterious agent which reduces the activity of at least one formulation by at least 10%, and then optionally exposed to steam, heat, H2, air, liquid water or other different substance (s) or condition(s) which increase the activity of at least one member of the collection by at least 10% over its previously-reduced activity whereby regenerability, reactivatability, decoking, or other catalyst property is measured. The deleterious agent can comprise elevated temperature, V, Pb, Ni, As, Sb, Sn, Hg, Fe, S or other metals, H2S, chlorine, oxygen, Cl, and/or carbon monoxide.

Reference to documents made in the specification is intended to result in such patents or literature being expressly incorporated herein by reference.

What is claimed is:

1. A parallel flow reactor for evaluating a plurality of differing compositions for catalysis, the reactor comprising a plurality of reaction channels arranged in an array with a density of at least 9 reaction channels per square inch, each of the plurality of reaction channels comprising an inlet for receiving a reactant-containing stream and an outlet for discharging a product-containing stream, and a plurality of catalyst-candidates having differing compositions, each of the plurality of catalyst candidates being in its own reaction channel, the reactor being adapted such that the reactant-containing stream can be fed through the plurality channels to simultaneously contact the catalyst candidates under reaction conditions that include a temperature greater than 100° C., and additionally, or alternatively, a pressure of greater than 1 bar.

2. A parallel flow reactor for evaluating a plurality of differing compositions for catalysis, the reactor comprising a plurality of reaction channels arranged in an array with a density of at least 9 reaction channels per square inch, each of the plurality of reaction channels comprising an inlet for receiving a reactant-containing stream and an outlet for discharging a product-containing stream, and a plurality of catalyst-candidates having differing compositions, each of the plurality of catalyst candidates being a metal or a metal-complex in its own reaction channel, the reactor being adapted such that the reactant-containing stream can be fed through the plurality channels to simultaneously contact the catalyst candidates under reaction conditions.

3. The parallel flow reactor of claims 1 or 2 further comprising a sampling system for sampling the product-containing streams of each of the plurality of reaction channels.

4. The parallel flow reactor of claims 1 or 2 further comprising a manifold comprising an array of tubes for sampling the product-containing streams of each of the plurality of reaction channels.

5. The parallel flow reactor of claims 1 or 2 further comprising a sensor for detecting catalytic activity of the candidate catalysts, an array of tubes for sampling the product-containing streams of each of the plurality of reaction channels, and an arrangement of switching valves for introducing the product-containing streams into the sensor.

6. An apparatus for evaluating a plurality of differing compositions for catalysis, the apparatus comprising a plurality of reaction channels arranged in an array, each of the plurality of reaction channels comprising an inlet for receiving a reactant-containing stream and an outlet for discharging a product-containing stream, a plurality of catalyst-candidates having differing compositions, each of the plurality of catalyst candidates being in its own reaction channel, the apparatus being adapted such that the reactant-containing stream can be fed through the plurality channels to simultaneously contact the catalyst candidates under reaction conditions that include a temperature greater than 100° C., and additionally, or alternatively, a pressure of greater than 1 bar, a plurality of sensors for detecting catalytic activity of the candidate catalysts, and a plurality of sampling tubes providing fluid communication between the plurality of reaction channels and the plurality of sensors for simultaneous, multistream detection of a reaction product in each of the plurality of discharged product-containing streams, each of the plurality of sensors being selected from the group consisting of a spectrometer and a chromatograph.

7. The parallel flow reactor of claims 1, 2, or 6 wherein the plurality of catalyst candidates are hydrocarbon conversion catalysts.

8. The parallel flow reactor of claims 1, 2 or 6 wherein at least twenty-four reaction channels comprise at least twenty-four catalyst candidates having differing compositions, each of the at least twenty-four catalyst compositions being in its own reaction channel.

9. The parallel flow reactor of claims 1, 2 or 6 wherein the plurality of reaction channels are arranged in an array with a density of at least 25 reaction channels per square inch.

10. The parallel flow reactor of claims 1, 2 or 6 wherein the plurality of reaction channels are circular or square in cross-section.

11. The parallel flow reactor of claims 1, 2 or 6 wherein the plurality of reaction channels are defined by tubes or pores.

12. The parallel flow reactor of claims 1, 2 or 6 further comprising a fluid distribution system for providing uniform flow of the reactant-containing stream through each of the plurality of reaction channels.

13. The parallel flow reactor of claims 1 or 6 wherein the plurality of catalyst candidates are inorganic catalysts.

14. The parallel flow reactor of claims 1 or 6 wherein the plurality of catalyst candidates are metals or metal oxides.

15. The parallel flow reactor of claims 1 or 6 wherein the plurality of catalyst candidates are transition metals or transition metal oxides.

16. The parallel flow reactor of claims 1 or 6 wherein the plurality of catalyst candidates are zeolites.

17. The parallel flow reactor of claims 1 or 6 wherein the plurality of catalyst candidates are supported catalysts.

18. The parallel flow reactor of claims 1 or 6 wherein each of the plurality of reaction channels further comprises a porous retaining mesh to keep the candidate catalysts in place in the reaction channel.

19. A parallel flow reactor for evaluating a plurality of differing compositions for catalysis, the reactor comprising a plurality of reaction channels in a monolithic support, each of the plurality of reaction channels comprising an inlet for receiving a reactant-containing stream and an outlet for discharging a product-containing stream, and a plurality of catalyst-candidates having differing compositions, the plurality of reaction channels being at least partially coated with the catalyst candidates such that each of the plurality of catalyst candidates is in its own reaction channel, the reactor being adapted such that the reactant-containing stream can be fed through the plurality channels to simultaneously contact the plurality of catalyst candidates under reaction conditions that include a temperature greater than 100° C., and additionally, or alternatively, a pressure of greater than 1 bar.

20. An apparatus for preparing and evaluating a plurality of differing compositions for catalysis, the apparatus comprising an automated liquid handling system for preparing a plurality of candidate catalysts or candidate catalyst precursors having different compositions, a monolithic support comprising a plurality of reaction channels for receiving the plurality of candidate catalyst or candidate catalyst precursors from the automated liquid handling system, the plurality of reaction channels being arranged in an array with a density of at least 9 reaction channels per square inch, and a parallel flow reactor adapted to evaluate the candidate catalysts on the monolithic support and configured such that each of the plurality of reaction channels comprises an inlet for receiving a reactant-containing stream and an outlet for discharging a product-containing stream, and a plurality of catalyst-candidates having differing compositions, each of the plurality of catalyst candidates being in its own reaction channel, the reactor being adapted such that the reactant-containing stream can be fed through the plurality channels to simultaneously contact the plurality of catalyst candidates under reaction conditions that include a temperature greater than 100° C., and additionally, or alternatively, a pressure of greater than 1 bar.

21. An apparatus for evaluating a plurality of differing compositions for catalysis, the apparatus comprising an automated liquid handling system for preparing a plurality of candidate catalysts or candidate catalyst precursors having different compositions, a monolithic support comprising a plurality of reaction channels for receiving the plurality of candidate catalyst or candidate catalyst precursors from the automated liquid handling system, and a parallel flow reactor adapted to evaluate the candidate catalysts on the monolithic support and configured such that each of the plurality of reaction channels comprises an inlet for receiving a reactant-containing stream and an outlet for discharging a product-containing stream, a plurality of catalyst-candidates having differing compositions, each of the plurality of catalyst candidates being in its own reaction channel, a plurality of sensors for detecting catalytic activity of the candidate catalysts, and an array of tubes for sampling the product-containing streams of each of the plurality of reaction channels, the sampling tubes being in fluid communication with the plurality of sensors for simultaneous, multistream detection of a reaction product in each of the plurality of discharged product-containing streams, the reactor being adapted such that the reactant-containing stream can be fed through the plurality channels to simultaneously contact the plurality of catalyst candidates under reaction conditions that include a temperature greater than 100° C., and additionally, or alternatively, a pressure of greater than 1 bar.

22. The apparatus of claims 6 or 21 wherein the sensors are selected from the group consisting of a mass spectrometer and a gas chromatograph.

23. The apparatus of claims 6 or 21 wherein the sensor is selected from the group consisting of a gas chromatograph, a temperature sensor, an optical monitor and a spectrometer.

24. An apparatus for evaluating a plurality of differing compositions for catalysis, the apparatus comprising the parallel flow reactor of claims 1, 2, 19, 20 or 21 and a sensor for detecting catalytic activity in candidate catalysts.

25. The apparatus of claim 24 wherein the sensor is selected from the group consisting of a gas chromatograph, a temperature sensor, an optical monitor and a spectrometer.

26. The parallel flow reactor of claim 25 wherein the optical monitor is an infrared detector.

27. The apparatus of claim 24 wherein the reactor further comprises an array of tubes for introducing a detection agent to the product-containing streams.

28. A parallel flow reactor for evaluating a plurality of differing compositions for catalysis, the reactor comprising
   a plurality of reaction channels in a monolithic support, each of the plurality of reaction channels comprising an inlet for receiving a reactant-containing stream, a well adjacent the channel for containing a candidate catalyst, and an outlet for discharging a product-containing stream,
   a plurality of catalyst-candidates having differing compositions, each of the plurality of catalyst candidates being in the well of its own reaction channel,
   a distribution system for providing uniform flow of the reactant-containing stream through each of the plurality of reaction channels, such that the reactant-containing stream simultaneously contacts the catalyst candidates under reaction conditions that include a temperature greater than 100° C., and additionally, or alternatively, a pressure of greater than 1 bar, and
   a sensor for detecting catalytic activity of the candidate catalysts.

29. The parallel flow reactor of claim 28 wherein each of the plurality of reaction channels further comprises a porous retaining mesh installed to keep the candidate catalyst in place.

30. The parallel flow reactor of claim 28 wherein the candidate-catalyst-containing well is at the bottom of each of the plurality of reaction channels.

31. A parallel flow reactor for evaluating a plurality of differing compositions for catalysis, the reactor comprising
   a plurality of reaction channels in a monolithic support, each of the plurality of reaction channels comprising an inlet for receiving a reactant-containing gas stream, an outlet for discharging a product-containing gas stream, and a porous retaining mesh to keep a candidate catalyst in place in the reaction channels,
   a plurality of catalyst-candidates having differing compositions, each of the plurality of catalyst candidates being a supported metal or a metal oxide catalyst in its own reaction channel,
   a distribution system adapted for providing uniform flow of the reactant-containing gas stream through each of the plurality of reaction channels, such that the reactant-containing gas stream simultaneously contacts the catalyst candidates under reaction conditions that include a temperature greater than 100° C., and additionally, or alternatively, a pressure of greater than 1 bar,
   an array of tubes for sampling the product-containing gas streams of each of the plurality of reaction channels,
   an arrangement of switching valves for introducing the product-containing streams into a sensor, and
   a sensor for detecting catalytic activity of the candidate catalysts.

32. An apparatus for preparing and evaluating a plurality of differing compositions for catalysis, the apparatus comprising
   an automated liquid handling system for preparing a plurality of candidate catalysts or candidate catalyst precursors having different compositions,
   a monolithic support for receiving the plurality of candidate catalysts or candidate catalyst precursors from the automated liquid handling system, and
   the parallel flow reactor of claims 2, 6, 19, 21, 28 or 31 adapted to evaluate the candidate catalysts on the monolithic support.

33. A parallel flow reactor for evaluating a plurality of differing compositions for catalysis, the reactor comprising
   a plurality of reaction channels, each of the plurality of reaction channels comprising an inlet for receiving a reactant-containing gas stream and an outlet for discharging a product-containing gas stream,
   a plurality of catalyst-candidates having differing compositions, each of the plurality of catalyst candidates being a supported metal or a metal oxide catalyst in its own reaction channel, each of the plurality of reaction channels being at least partially coated with the candidate catalysts,
   a distribution system adapted for providing uniform flow of the reactant-containing gas stream through each of the plurality of reaction channels, such that the reactant-containing gas stream simultaneously contacts the catalyst candidates under reaction conditions that include a temperature greater than 100° C., and additionally, or alternatively, a pressure of greater than 1 bar,
   an array of tubes for sampling the product-containing gas streams of each of the plurality of reaction channels,
   a sensor for detecting catalytic activity of the candidate catalysts, and optionally,
   an arrangement of switching valves for introducing the product-containing streams into the sensor.

34. A method for evaluating a plurality of differing compositions for catalysis, the method comprising
   flowing a reactant-containing stream through each of a plurality of reaction channels in a parallel flow reactor of claims 1, 2, 6, 19, 21, 28, 31 or 33 to simultaneously contact the catalyst candidates under the reaction conditions, and
   sensing a product-containing stream to detect catalytic activity of the plurality of candidate catalysts.

35. The method of claim 34 further comprising
   depositing a plurality of catalyst precursors to the plurality of reaction channels, each of the plurality of catalyst precursors being in its own reaction channel,
   drying, and additionally, or alternatively, calcining the catalyst precursors in the reaction channels to form the catalyst candidates.

* * * * *